United States Patent
Day

(10) Patent No.: US 10,905,400 B2
(45) Date of Patent: Feb. 2, 2021

(54) APPARATUS AND METHOD FOR OPTIMIZATION OF ULTRASOUND IMAGES

(71) Applicant: Toshiba Medical Systems Corporation, Otawara (JP)

(72) Inventor: Timothy Day, Edinburgh (GB)

(73) Assignee: Canon Medical Systems Corporation, Otawara (JP)

( * ) Notice: Subject to any disclaimer, the term of this patent is extended or adjusted under 35 U.S.C. 154(b) by 858 days.

(21) Appl. No.: 14/628,786

(22) Filed: Feb. 23, 2015

(65) Prior Publication Data

US 2016/0242740 A1 Aug. 25, 2016

(51) Int. Cl.
*A61B 8/08* (2006.01)
*A61B 8/14* (2006.01)
(Continued)

(52) U.S. Cl.
CPC .......... *A61B 8/5207* (2013.01); *A61B 8/0866* (2013.01); *A61B 8/14* (2013.01);
(Continued)

(58) Field of Classification Search
CPC .................. A61B 8/0866; A61B 8/483; G06T 2207/30044; G06T 2207/10136
See application file for complete search history.

(56) References Cited

U.S. PATENT DOCUMENTS 6,102,861 A 8/2000 Avila et al.
8,556,814 B2 10/2013 Monteiro De Barros Carneiro et al.
(Continued)

FOREIGN PATENT DOCUMENTS

JP 2000-325346 A 11/2000
JP 2001-017426 A 1/2001
(Continued)

OTHER PUBLICATIONS

Feng et al., "Automatic Fetal Face Detection From Ultrasound Volumes Via Learning 3D and 2D Information." 2009 IEEE. pp. 2488-2495.*
(Continued)

*Primary Examiner* — James M Kish
(74) *Attorney, Agent, or Firm* — Oblon, McClelland, Maier & Neustadt, L.L.P.

(57) ABSTRACT

An ultrasonic imaging apparatus comprises a volume data generating unit for generating volume data by processing echo signals obtained through ultrasonic transmission and reception to and from a three dimensional region including at least a portion of a body part. The ultrasonic imaging apparatus further comprises a rendering unit configured to generate a rendering image by performing a volume rendering process or a surface rendering process for the volume data based on a plurality of parameters, a display control unit for displaying image on a display unit, and a parameter adjustment unit for performing a detection of the at least a portion of the body part in the rendering image, and selecting or adjusting the value of at least one of the parameters based on a result of the detection, wherein said rendering unit is configured to generate a new rendering image based on the selected or adjusted parameter values from said parameter adjustment unit, and wherein said display control unit is configured to display said new rendering image on said display unit.

21 Claims, 6 Drawing Sheets

(51) Int. Cl.
*G06T 19/00* (2011.01)
*A61B 8/00* (2006.01)

(52) U.S. Cl.
CPC ............ *A61B 8/483* (2013.01); *A61B 8/5223* (2013.01); *G06T 19/00* (2013.01); *A61B 8/0883* (2013.01); *A61B 8/463* (2013.01); *A61B 8/467* (2013.01); *A61B 8/5269* (2013.01); *G06T 2207/10136* (2013.01); *G06T 2207/30044* (2013.01); *G06T 2210/41* (2013.01); *G06T 2219/008* (2013.01)

(56) References Cited

U.S. PATENT DOCUMENTS

| | | | | |
|---|---|---|---|---|
| 2003/0152262 | A1* | 8/2003 | Mao | G06K 9/3233 382/154 |
| 2009/0009514 | A1* | 1/2009 | Pagoulatos | A61B 8/13 345/424 |
| 2011/0077516 | A1 | 3/2011 | Abe | |
| 2014/0152661 | A1* | 6/2014 | Nishiura | G06T 15/08 345/424 |
| 2015/0116323 | A1* | 4/2015 | Buckton | G06T 19/00 345/424 |

FOREIGN PATENT DOCUMENTS

| | | |
|---|---|---|
| JP | 2011-072656 A | 4/2011 |
| JP | 2013-017669 A | 1/2013 |

OTHER PUBLICATIONS

Nelson et al., "Three-dimensional ultrasound of fetal surf ace features." Ultrasound Obstet. Gynernl. 2 ( 1992), pp. 166-174.*
Tom Mitchell, "CMU Face Images Data Set", UCI Machine Learning Repository, Sep. 3, 2014, 2 Pages http://archive.ics.uci.edu/ml/datasets/CMU+Face+Images.
Shaolei Feng, et al., "Automatic Fetal Face Detection From Ultrasound Volumes Via Learning 3D and 2D Information", Computer Vision and Pattern Recognition, IEEE, 2009, pp. 2488-2495.
"Viola-Jones object detection framework", Wikipedia, retrieved Dec. 18, 2014, 7 pages http://en.wikipedia.ora/wiki/Viola%E2%80%93Jones_object_detection_framework.
"Boosting methods for object categorization", Wikipedia, retrieved Dec. 18, 2014, 3 Pages http://en.wikipedia.org/wiki/Boosting_methods_for_object_categorization.
Christian Szegedy, "Building a deeper understanding of images", Google Research Blog, Sep. 5, 2014, 9 Pages http://googleresearch.blogspot.co.uk/2014/09/building-deeper-understanding-of-images.html.
"Toshiba Launches New Line-up of Image Recognition Processors for Automatic Applications", Toshiba press release, Nov. 13, 2014, 5 pages http://www.mynewsdesk.com/toshiba-global/pressreleases/toshiba-launches-new-line-up-of-image-recoonition-processors-for-automotive-applications-tmpv760-seriesenables-night-time-pedestrian-detection-1083381.
Thanh-Toan Do, et al., "Face Recognition Using Co-Occurence Histograms of Oriented Gradients", International Conference on Acoustics, Speech, and Signal Processing, ICASSP, Mar. 2012, 5 Pages.
Shehroz S. Khan, et al., "Evaluating Visual Aesthetics in Photographic Portraiture", Computational Aesthetics in Graphics, Visualization and Imaging, 2012, 8 Pages.
"Carestream Touch Ultrasound", Carestream, retrieved Feb. 11, 2015, 2 Pages http://www.carestream.com/touch.html.
Bill Smith, "The Practical Application and Clinical Use of Modern 3D Ultrasound Technology in Gynaecology", Toshiba Leading Innovation, retrieved Dec. 18, 2014, 13 pages http://www.toshiba-medical.eu/eu/wp-content/uploads/sites/2/2014/06/WP_TWPUS0012EC_Smith_3D-US.pdf.
"Face detection using Haar Cascades", Open-CV Python Tutorials, OpenCV 3.0.0-dev documentation, retrieved Feb. 11, 2015, 3 Pages, http://docs.opencv.org/trunk/doc/py_tutorials/py_objdetect/py_face_detection/py_face_detection.html.
"Package: python-opencv (2.3.1-11) Python bindings for the computer vision library", Debian, retrieved Feb. 11, 2015,4 Pages https://packages.debian.org/wheezy/python-opencv.
Dolores H. Pretorius, et al., "Preexamination and Postexamination Assessment of Parental-Fetal Bonding in Patients Undergoing 3-/4-Dimensional Obstetric Ultrasonography", J. Ultrasound Med., Nov. 1, 2006, vol. 25, No. 11, pp. 1411-1421.

* cited by examiner

APPARATUS AND METHOD FOR OPTIMIZATION OF ULTRASOUND IMAGES

FIELD

Embodiments described herein relate generally to a method of, and apparatus for, optimization of ultrasound images, for example optimization of fetal ultrasound images comprising a representation of a face, hand, foot or other body part.

BACKGROUND

It is known to use ultrasound to image a fetus in the womb by transmission and reception of ultrasound waves from a transducer.

Three-dimensional (3D) ultrasound images may be obtained by using software to combine ultrasound data that has been taken at different positions or angles, and to render an image from the combined data using methods such as simple surface shading or direct volume rendering. In four-dimensional (4D) ultrasound imaging systems, a series of three-dimensional images obtained at different times is dynamically rendered to produce a moving 3D image, for example a 3D ultrasound movie.

In recent years, 3D and 4D ultrasound images have been made more realistic through the use of advanced lighting techniques (referred to as global illumination, gradient free lighting, subsurface scattering or photon mapping) that simulate illumination with a more physically accurate model than was previously used.

A popular objective of 3D and 4D fetal ultrasound scans (sometimes known as fetal keepsake scans) is to image the fetal face. Many parents have 3D or 4D ultrasound scans in order to bond better with their unborn child, motivated by the realistic appearance of the scans. 3D or 4D ultrasound scans can also be useful for informing parents of the appearance of a fetus that has an abnormality such as a cleft lip or cleft palate.

3D and 4D ultrasound scans may also be performed on other parts of the human or animal body, for example on internal organs.

An example of a 3D ultrasound fetal imaging process is represented schematically in the diagram of FIG. 1. A sonographer 30 operates an ultrasound measurement probe 4 to scan a patient 32 who is carrying a fetus 34.

A volume data generating unit 18 performs echo processing, volume reconstruction and filtering on echo signals obtained from measurement probe 4. The volume data generating unit 18 outputs volume data. A rendering unit 14 renders an image 50 from the volume data and the image 50 is displayed on main display screen 6.

The processing, rendering, and image display is repeated as further echo signals are received at measurement probe 4. The fetus may be moving while images are taken.

To obtain a good quality image of the fetal face, the sonographer 30 may be required to optimize the position of the probe 4 to obtain the best signal and volume data. While adjusting the position and orientation of probe 4, the sonographer 30 may also adjust values for at least some of a set of parameters 40 using scanner console 10.

The set of parameters 40 may include processing parameters (for example, parameters used by the volume data generating unit 18 in the processing of echo signals to obtain volume data). For example, the sonographer 30 may optimize ultrasound reconstruction and filtering controls to obtain the best trade-off between the visibility of fine details versus the level of noise in the image.

The set of parameters 40 may include rendering parameters (for example, parameters used by the rendering unit 14 in the rendering of volume data to form an image, for example an image for display). The sonographer 30 may optimize the rendering viewpoint to best reveal the facial features. The visibility of eyes, nose and mouth may be considered to be particularly crucial.

The sonographer 30 may sculpt the image to avoid features that may obscure the face in the image and/or position the viewpoint to avoid features that may obscure the face in the image. Such potentially obscuring features may include detritus, the placenta/cord, or the womb walls. The sonographer 30 may vary a clip plane position to remove matter in front of the face.

Advanced rendering modes may introduce more potentially controllable rendering parameters. For example, optical properties of tissues, shading model parameters and light positioning may become more important than in conventional surface shaded rendering.

If the sonographer 30 decides that the displayed image 50 is not of adequate quality (for example, only part of the face is displayed, or the face is upside-down) then the sonographer 30 may adjust values for at least some of the set of parameters 40 and/or adjust the position or orientation of the measurement probe 4 to attempt to obtain an improved image.

It can be difficult for a sonographer to simultaneously find and maintain the probe 4 in an optimum or acceptable position, whilst also selecting or adjusting rendering and/or processing parameters to obtain a displayed image of acceptable quality. This may particularly be the case in practical situations in which the fetus and the mother may be moving during the ultrasound scan process.

It has been suggested to use a learning approach to detect a three-dimensional face surface in volumetric ultrasound data. In one example, a mesh representation of the three-dimensional face surface is used. Candidate facial boundary boxes are obtained using a marginal space learning method and are refined using two-dimensional face profile detection. A mean shape is then deformed to the face shape. Results of the face surface detection are used to determine a particular acquisition plane for face rendering. For example, an image may be rendered at a particular viewing angle with respect to the fetal face. Results of the face surface detection are used by a carving algorithm to carve out voxels in front of the face.

Such a learning approach may require locating many mesh points on the face surface in three dimensions. Locating all the mesh points in three dimensions is a complex problem given that the fetus may be at any position and at any angle within the womb. It may be necessary to determine which anatomical features the mesh points correspond to, for example which mesh points are on the profile or at other landmarks such as the eyes, nose and mouth. The process of locating and identifying mesh points may be computationally intensive.

BRIEF DESCRIPTION OF THE DRAWINGS

Embodiments are now described, by way of non-limiting example, and are illustrated in the following figures, in which.

DETAILED DESCRIPTION

Certain embodiments provide an ultrasonic imaging apparatus comprising a volume data generating unit for generating volume data by processing echo signals obtained through ultrasonic transmission and reception to and from a three dimensional region including at least a portion of a body part. The apparatus also comprises a rendering unit configured to generate a rendering image by performing a volume rendering process or a surface rendering process for the volume data based on a plurality of parameters. The apparatus further comprises a display control unit for displaying images on a display unit. The apparatus further comprises a parameter adjustment unit for performing a detection of the at least a portion of the body part in the rendering image, and selecting or adjusting the value of at least one of the parameters based on a result of the detection. The rendering unit is configured to generate a new rendering image based on the selected or adjusted parameter values from said parameter adjustment unit. The display control unit is configured to display said new rendering image on said display unit.

Certain embodiments also provide an ultrasonic imaging method that comprises generating volume data by processing echo signals obtained through ultrasonic transmission and reception to and from a three dimensional region including at least a portion of a body part. The method also comprises generating a rendering image by performing a volume rendering process or a surface rendering process for the volume data based on a plurality of parameters, and performing a detection of the at least a portion of the body part in the rendering image. The method further comprises selecting or adjusting the value of at least one of the parameters based on a result of the detection, generating a new rendering image based on the selected or adjusted parameter values, and displaying the new rendering image on a display unit.

A rendering image may also be referred to a rendered image.

Figure 2:
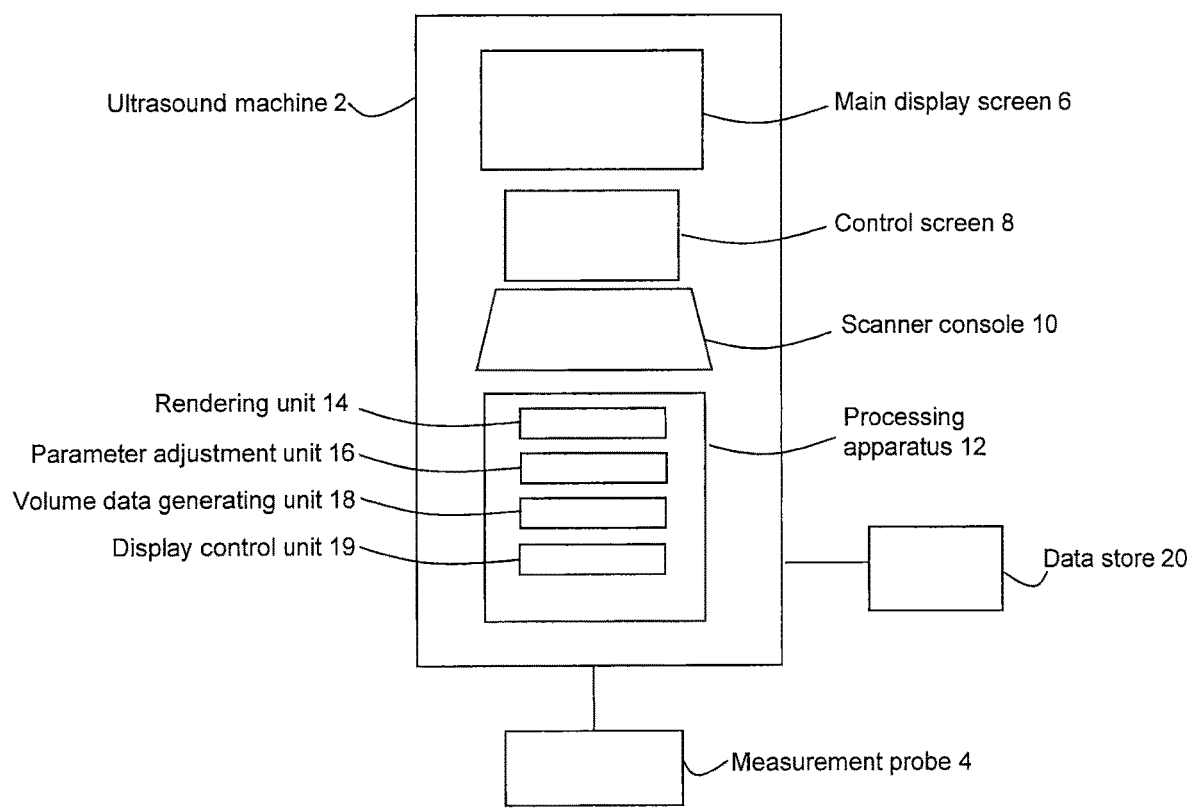
FIG. 2 is a schematic diagram of an apparatus according to an embodiment.

An ultrasound imaging apparatus (which may also be called an ultrasound diagnostic apparatus) according to an embodiment is illustrated schematically in FIG. 2. The apparatus comprises an ultrasound machine 2 and an associated measurement probe 4. Any suitable type of ultrasound machine 2 and measurement probe 4 may be used, for example any ultrasound machine 2 and transducer probe 4 that are configured to obtain ultrasound image data that is suitable for 3D or 4D imaging.

The ultrasound machine 2 comprises a main display screen 6 for displaying a main ultrasound image, a control screen 8 for displaying control information (for example, parameter settings), and a scanner console 10. In this embodiment, the scanner console 10 comprises an input device or devices such as input buttons or knobs, a computer keyboard, a mouse or a trackball. In alternative embodiments, the control screen 8 is a touch screen, which is both a display device and a user input device. Further embodiments may comprise a control screen 8, display screen or main display screen 6 that does not form part of the ultrasound machine 2.

The ultrasound machine 2 comprises a processing apparatus 12 for processing of data, including image data. The processing apparatus 12 includes a rendering unit 14 for rendering images, and a parameter adjustment unit 16 for performing face detection.

The processing apparatus 12 also comprises a volume data generating unit 18 which is configured to process echo signals received from measurement probe 4 and a display control unit 19 which is configured to display images on main display screen 6.

The rendering unit 14, parameter adjustment unit 16, volume data generating unit 18 and display control unit 19 are each implemented in processing apparatus 12 by means of a computer program having computer-readable instructions that are executable to perform the method of the embodiment. However, in other embodiments each unit may be implemented in software, hardware or any suitable combination of hardware and software. In some embodiments, the various units may be implemented as one or more ASICs (application specific integrated circuits) or FPGAs (field programmable gate arrays).

Figure 1:
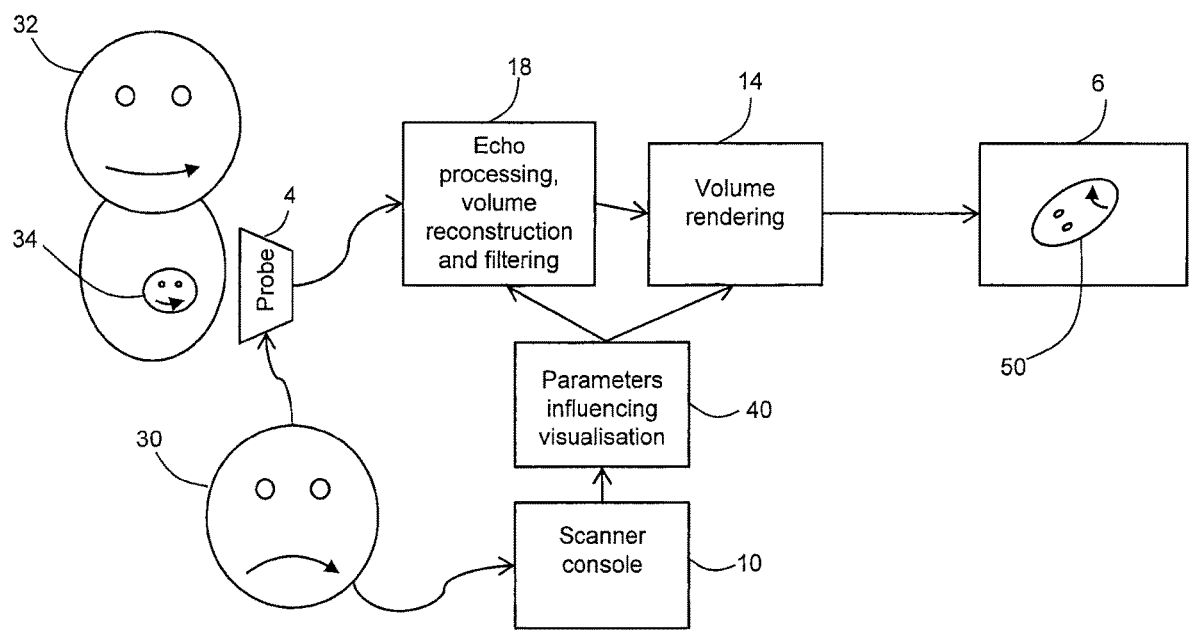
FIG. 1 is a schematic diagram of an ultrasound process.

The processing apparatus 12 also includes a hard drive and other components including RAM, ROM, a data bus, an operating system including various device drivers, and hardware devices including a graphics card. Such components are not shown in FIG. 1 for clarity. In an alternative embodiment, the processing apparatus 12 is not part of the ultrasound machine 2 and may be, for example, a personal computer, workstation, tablet, mobile phone and/or mobile computing apparatus.

In the present embodiment, the system of FIG. 2 is used to perform a scan of a patient 32 who is carrying a fetus 34, to render images of the fetal face from volume data generated from the scan, to perform face detection on each rendered image and provide a score for each rendered image dependent on the image quality of the face detected, and to select image orientation parameters based on the scores for the images.

In other embodiments, the system of FIG. 2 may be used to render images of any desired body part of a fetus (for example, a fetal face, hand or foot), perform detection of the desired body part in the rendered images and provide a score for each of the rendered images based on the detection, and select any appropriate image processing or rendering parameter based on the scores.

In further embodiments, the system of FIG. 2 may be used to render images of a body part that is not part of a fetus. The system of FIG. 2 may be used to render images of an internal organ, for example, a heart or kidney. The system of FIG. 2 may be used in gynecological applications, for example to render images of a uterus or ovary. The system of FIG. 2 may be used to perform detection of the internal organ in the rendered images and provide scores for the rendered image, and select any appropriate image processing or rendering parameter based on the scores.

Figure 3:
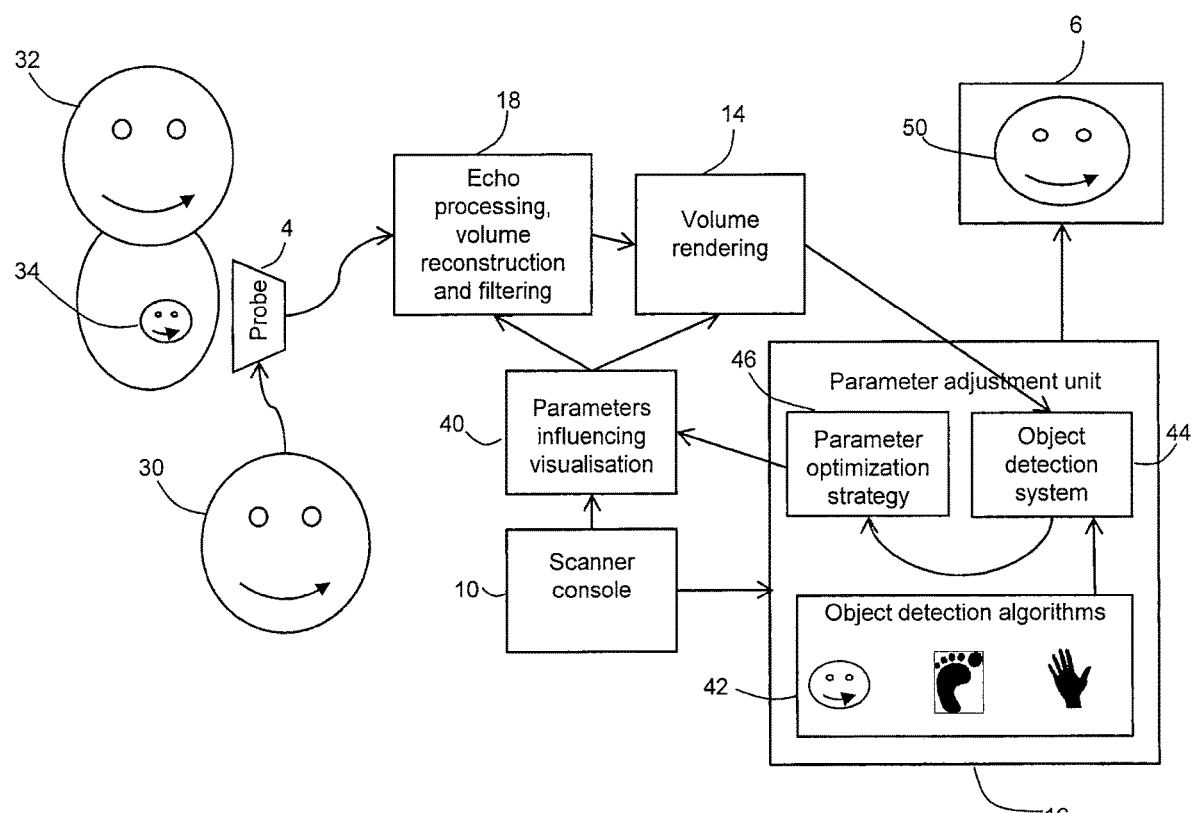
FIG. 3 is a schematic diagram of an ultrasound process according to an embodiment.

A mode of operation of the system of FIG. 2 in the present embodiment is illustrated in overview in the diagram of FIG. 3.

A sonographer 30 operates the ultrasound measurement probe 4 to scan a patient 32 who is carrying a fetus 34, in order to obtain an image of the fetal face. The sonographer 30 places the probe 4 on the abdomen of the patient 32. The operation of the probe 4 may include adjusting the position and orientation of the measurement probe 4 on the abdomen of the patient 32.

The control screen 8 displays values for at least some of a set of parameters 40. Parameters in the set of parameters 40 comprise parameters that influence visualization of ultrasound data. The set of parameters 40 includes processing parameters (which may be parameters used in the processing of echo signals to obtain volume data) and rendering parameters (which may be parameters used in the rendering of volume data to form an image).

In the present embodiment, each parameter in the set of parameters 40 has an initial value that is set automatically. In the present embodiment, the sonographer 30 does not adjust any of the values for the parameters while operating the probe 4. In other embodiments, the sonographer 30 adjusts values for one or more of the parameters while operating the probe 4.

In the present embodiment, the control screen 8 displays values for at least some of the set of parameters 40. In other embodiments, values for the set of parameters 40 may not be displayed.

The volume data generating unit 18 receives echo signals from the measurement probe 4 while the probe 4 is being operated by the sonographer 30. Values for processing parameters from the set of parameters 40 are passed to the volume data generating unit 18. In the present embodiment, the values for the processing parameters are the initial values that are set automatically in the system. In other embodiments, the values for one or more of the processing parameters may have been set by the sonographer 30 before or during the operation of the probe 4.

The processing parameters comprise echo-processing control parameters, reconstruction parameters, signal parameters, volume parameters, and filtering parameters. The volume data generating unit 18 uses the processing parameter values in performing echo processing, volume reconstruction and filtering on the echo signals to obtain volume data. The volume data generating unit 18 outputs the volume data to a rendering unit 14.

The rendering unit 14 receives values for rendering parameters from the set of parameters 40. In the present embodiment, the values for the rendering parameters are the initial values that are set automatically in the system. In other embodiments, the values for one or more of the processing parameters may have been set by the sonographer 30 before or during the operation of the probe 4. The rendering parameters comprise rendering orientation parameters, lighting parameters and optical properties.

The rendering unit 14 and parameter adjustment unit 16 perform an image optimization as described below.

In a first part of the image optimization, the rendering unit 14 renders a plurality of rendering images from the volume data. The rendering unit 14 renders one rendering image using the rendering parameter values that were received from the set of parameters 40. The rendering unit 14 renders the other rendering images using rendering parameter values that are obtained by varying at least one of the received rendering parameter values, such that each of the rendering images is rendered using different rendering parameter values.

The rendering of each rendering image comprises generating a rendering image data set that is representative of the rendering image. Each rendering image may be described as a 3D image, because it is an image that, when viewed, gives the impression of the surface of a structure (here, the fetus) in three dimensions. However, the image is itself represented by two dimensional data. For example, each rendering image data set may comprise a set of pixel positions with associated intensity values and/or color values (for example, RGB or HSL values). The rendering images do not have to be displayed on the display screen at this stage of the process, although in some embodiments they can be displayed if so desired.

The rendering image data sets that are representative of the rendering images are passed to the parameter adjustment unit 16. The parameter adjustment unit 16 comprises an object detection system 44 which uses an object detection algorithm 42. In the present embodiment, the object detection algorithm 42 is a face detection algorithm.

In a second part of the image optimization, parameter adjustment unit 16 uses the face detection algorithm to perform a face detection on each of the rendering images, by applying the face detection algorithm to the rendering image data sets. The face detection algorithm returns a score (which may be described as a value for a quality measure) for each of the rendering image data sets. The score depends on how good a representation of a face (as quantified by the face detection algorithm) is found in the rendering image data set. If a face is found that is of low quality (for example, the face is partially obscured, of low resolution, and/or rotated away from the viewing angle), then it is likely that the score is will be lower than if a good-quality representation of a face is found (for example, the whole face is shown facing the viewing angle and the image is of good resolution).

The parameter adjustment unit 16 selects the rendering image data set that has the highest face detection score (and therefore may be expected to correspond to the best facial image as determined by the face detection algorithm). The display control unit 19 displays on main display screen 6 the rendering image 50 corresponding to the selected rendering image data set.

The parameter adjustment unit 16 determines values for at least some of the parameters from the selected rendering image data set. The determination of the parameter values may be described as an optimization of parameter values or parameter optimization strategy 46.

In the present embodiment, the parameter adjustment unit 16 determines a respective value for each parameter in a set of rendering parameters by selecting the value for that parameter that was used in rendering the selected rendering image data set.

The parameter adjustment unit 16 updates the values for the set of parameters 40 so that the values for at least some of the rendering parameters in the set of parameters 40 are replaced by the determined values for those parameters.

In some cases, the selected rendering image data set is a rendering image data set that was obtained by varying a value of one of the rendering parameters (for example, a lighting angle) such that the rendering is performed using a value of said rendering parameter that is different from the received value. The parameter adjustment unit 16 updates the value for that rendering parameter (for example, the lighting angle) to the value that was used in rendering the selected rendering image data set.

In other cases, the selected rendering image data set is the rendering image data set that was rendered using the set of rendering parameters that were received from the set of parameters 40, and therefore the determined values for the rendering parameters are the same as the initial values.

The resulting updated rendering parameter values are used in the rendering of subsequent ultrasound data. Therefore, rendering parameters of the rendering image data set that was selected as having the best face detection score are used in the rendering of subsequent volume data. The rendering parameters are updated in real time while the sonographer 30 is operating the probe 4 to scan the abdomen of the patient 32.

An embodiment in which the determined rendering parameters are rendering orientation parameters is described in greater detail below with reference to the flowchart of FIG. 4.

Figure 4:
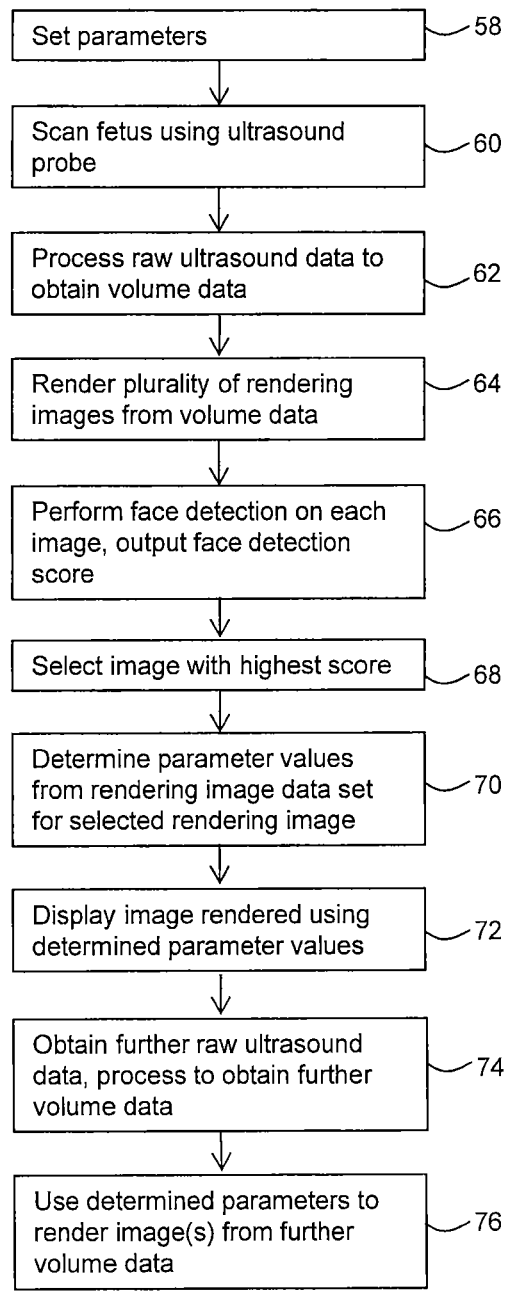
FIG. 4 is a flowchart illustrating in overview a mode of operation of an embodiment.

The flowchart of FIG. 4 describes an embodiment in which the sonographer 30 is scanning a patient 32 to obtain an image of the face of the fetus 34. The process described with reference to FIG. 4 comprises an optimization of rendering orientation parameters to obtain the best possible image of the face of the fetus 34. The optimization may involve adjusting rendering orientation parameters, for example roll and yaw angles, to change the direction of rendering to obtain a desired rendering direction relative to the fetal face.

At stage 58, values for a number of parameters relating to an ultrasound process are determined before starting an ultrasound scan. The parameters include processing parameters (for example, one or more of echo processing parameters, reconstruction parameters and filtering parameters, gain, acoustic power, frequency, threshold, sweep angle, resolution, and/or focus) and rendering parameters (for example, rendering orientation parameters, lighting angle and shading parameters).

In the present embodiment, values for the parameters are set by a sonographer 30 using scanner console 10 before the ultrasound scan is started. For example, the sonographer 30 may select a pre-programmed set of parameter values or the sonographer 30 may enter some or all of the parameter values manually. The sonographer 30 may select values for parameters or combinations of parameters from a selection, for example from a drop-down menu.

In other embodiments, the sonographer 30 does not enter parameter values before the ultrasound scan is started. In such embodiments, the determined parameter values at the start of the ultrasound scan may be default values held by the ultrasound machine 2 or processing apparatus 12.

At stage 60, the sonographer 30 scans the patient 32 who is carrying the fetus 34, using measurement probe 4 which is connected to ultrasound machine 2. The measurement probe 4 is configured to obtain three-dimensional raw ultrasound data by measuring reflected ultrasound energy at a range of angles. The raw ultrasound data is representative of echo signals obtained through ultrasound transmission and reception to and from a three-dimensional region that is expected to include at least a portion of the fetal face. Volume acquisition may be performed once, or may be repeated at successive time intervals.

A set of raw ultrasound data corresponding to a first time interval is obtained from the scan of stage 60.

At stage 62, the volume data generating unit 18 processes the set of raw ultrasound data to obtain a volume data set. The volume data comprises a three-dimensional representation of the scanned region of the patient. In the present embodiment, the processing of the raw ultrasound data comprises reconstruction and filtering, and the volume data set is a Cartesian image volume (having voxels in x, y, z coordinates rather than in the fan-beam configuration of the raw ultrasound data). In other embodiments, any suitable method of processing the raw ultrasound data from the measurement probe to obtain volume data may be used. The volume data set comprises a plurality of voxels with associated intensities.

In processing the raw ultrasound data, the volume data generating unit 18 uses the values of processing parameters that were determined at stage 58. In the present embodiment, the values for the processing parameters determined at stage 58 are values that were set by the sonographer 30 before the start of the ultrasound scan. In other embodiments, the values for the processing parameters determined at stage 58 may be default values for the ultrasound machine, or may have been determined by any suitable manual, automatic, or semi-automatic method. In the present embodiment, the processing parameters include echo processing parameters, reconstruction parameters and filtering parameters.

At stage 64, the rendering unit 14 performs a first part of an image optimization (which may also be referred to as an optimization of parameters). The rendering unit 14 receives the volume data set from the volume data generating unit 18. The rendering unit 14 processes the volume data set to obtain a plurality of rendering image data sets, each representative of a respective rendering image.

In the processing of the volume data set, the rendering unit 14 uses the rendering parameter values that were determined at stage 58. In the present embodiment, the rendering parameter values determined at stage 58 are values that were set by the sonographer 30 before the start of the ultrasound scan. In other embodiments, the rendering parameter values determined at stage 58 may be default values for the ultrasound machine, or may have been determined by any suitable manual, automatic, or semi-automatic method. In the present embodiment, the rendering parameters include rendering orientation parameters, lighting parameters and shading parameters. Rendering orientation parameters may be representative of the three-dimensional orientation of the image relative to a viewpoint. The rendering orientation parameters may include a viewing point and/or viewing direction. The rendering parameters also include an isosurface value.

In the present embodiment, the rendering unit 14 is configured to generate the rendering images by performing a surface rendering process for the volume data based on the plurality of parameters. To generate each of the rendering images, the rendering unit 14 determines a three-dimensional isosurface from voxels in the volume data that have values corresponding to the isosurface value. In the present embodiment, the isosurface is representative of the surface of the fetus. The rendering unit 14 constructs a representation of the isosurface, for example as a mesh or grid. The rendering unit 14 then renders an image of the isosurface and outputs a rendering image data set that is representative of the rendering image. Any appropriate surface rendering process may be used.

In other embodiments, the rendering unit 14 is configured to generate the rendering images by performing a volume rendering process for the volume data, for example by performing direct volume rendering or global illumination. For example, a color and opacity may be assigned to each voxel using a transfer function, and a volume rendering process may be used to render an image using the colors and opacities and to output a rendering image data set that is representative of the rendering image.

The rendering unit 14 generates one rendering image data set using the rendering parameter values that were determined at stage 58. The rendering unit 14 generates the rendering image data set using a surface rendering process in which the rendering orientation parameters, lighting parameters, shading parameters and isosurface value are those determined at stage 58. The rendering unit 14 determines a three-dimensional isosurface of voxels in the volume data that have intensity values corresponding to the isosurface value. The isosurface is representative of the surface of the fetus. The rendering image data set corresponds to an image of the isosurface viewed from the specified rendering orientation, with specified lighting parameters (for example, light position) and shading parameters.

The rendering image data set comprises color and/or intensity values for a two-dimensional array of pixels which are representative of a rendering image that may be displayed on a two-dimensional surface, for example on a display screen. The rendering image may in some circumstances be referred to as a three-dimensional image because it shows an isosurface representative of the three-dimensional surface of the fetus.

In the present embodiment, the display control unit 19 displays on the main display screen 6 the rendering image 50 that has been rendered using the received rendering parameters from stage 58. In other embodiments, this rendering image may not be displayed.

The rendering unit 14 renders additional rendering images using rendering parameter values that are based on those determined at stage 58, but with a variation of at least one of the parameter values, as described below.

Rendering orientation parameters are varied across the different rendering images, while other rendering parameters (for example, lighting position and shading parameters) are held constant. All the rendering images are rendered with the same lighting position and with the same shading parameters. It may be noted that any given volume data set (obtained from a given probe position and orientation) is capable of being rendered with many different orientations in three dimensions.

In the present embodiment, the rendering orientation parameters that are varied across different ones of the plurality of rendering images are roll angle and yaw angle. In other embodiments, a pitch angle may be used in addition to roll and yaw angles.

The rendering unit 14 receives the initial value for roll angle and the initial value for yaw angle that have been set at stage 58 (for example, by the sonographer 30 or as a default system value).

The rendering unit 14 selects a plurality of roll angles and a plurality of yaw angles by incrementing the initial values. In one example, the rendering unit 14 selects values for roll angle of initial value minus 30°, initial value minus 20°, initial value minus 10°, initial value, initial value plus 10°, initial value plus 20°, initial value plus 30°.

A rendering image is obtained for each combination of roll angle value and yaw angle value in the determined ranges. Each rendering image is represented by a respective rendering image data set In the present embodiment, the rendering unit 14 determines values for roll angle and yaw angle by incrementing an initial value for roll angle and incrementing an initial value for yaw angle. In other embodiments, the rendering unit 14 determines values for roll angle and yaw angle by referring to a list or table of values for roll angle and yaw angle. For example, the list or table may be populated by the sonographer 30 or may be stored as a system default. In other embodiments, the rendering unit 14 may determine a plurality of values for roll angle and a plurality of values for yaw angle using any suitable method.

Although the present embodiment increments values for roll angle and yaw angle, in other embodiments pitch angle may also be used. An alternative system of rendering orientation parameters may be used.

In alternative embodiments, other rendering parameters may be varied for the different rendering images. For example, each of the rendering images may be rendered with a different lighting position, or each of the rendering images may be rendered with a different value of shading.

At stage 66, the rendering unit 14 passes the rendering image data sets to the parameter adjustment unit 16. The parameter adjustment unit 16 performs a face detection on each of the volume rendering image data sets using a face detection algorithm. In the present embodiment, the parameter adjustment unit 16 performs a face detection using a face detection algorithm from the OpenCV image processing library. The face detection algorithm from the OpenCV image processing library uses a Viola-Jones object detection framework which uses cascades of boosted classifiers working with Haar-like simple features. The face detection algorithm from the OpenCV image processing library may be optimized by summed area tables, and therefore may be feasible for real-time operation in hardware with modest computing power (for example, some ultrasound scanners may have modest computing power). The face detection algorithm can be trained on a set of fetal faces.

In other embodiments, any suitable face detection method may be used. It is known to use face detection algorithms which can identify the presence of a face in an image, and/or locate the face in the image, and/or provide a measure of quality (for example, a measure of confidence, such as a measure of confidence that the image actually represents a face, or a measure of the alignment, symmetry or orientation of the face). Suitable face detection algorithms may comprise face detection algorithms that are based on neural networks or genetic algorithms. Suitable face detection algorithms may comprise face detection algorithms using co-occurrence histograms of oriented gradients.

Face detection algorithms are algorithms that can identify the presence or absence of a face or face-like features in an image. Face recognition algorithms (that can be used to detect particular individuals) are also known. The method of the present embodiment uses face detection (determination that a face is present).

Although the face detection algorithm may be described as acting on an image (for example on a rendering image), the face detection algorithm operates on a two-dimensional image data set that is representative of the image, for example a two-dimensional image data set comprising an array of pixel locations and associated pixel intensities. The rendering image data sets are such two-dimensional image data sets. It is not necessary that a rendering image be displayed when performing face detection on the rendering image by applying the face detection algorithm to the rendering image data set that is representative of that rendering image.

The parameter adjustment unit 16 runs the face detection algorithm on each of the rendering image data sets. For each rendering image data set, the face detection algorithm returns a location and score for each candidate face in the image data set. The face detection algorithm may return a location by returning the coordinates of a two-dimensional box in the two-dimensional space of the rendering image data set.

The Viola-Jones object detection framework measures how well a candidate face matches successive sets of Haar features. If the candidate face is well matched to the sets of Haar features, a high score is returned. The Viola-Jones framework is trained such that a clear face that is fully facing the direction at which it is viewed should return a high score, and partial or less clear faces should return a lower score.

The parameter adjustment unit 16 compares each score to a threshold value. The threshold value is used to separate results that are considered to be faces from results that are considered not to be faces. If the score does not meet the threshold value, the parameter adjustment unit 16 does not consider the candidate face further.

For a given rendering image data set, the face detection algorithm may return zero, one, or more than one candidate faces. If the face detection algorithm returns more than one candidate face, the parameter adjustment unit 16 selects the candidate face with the highest score.

The score may be considered to be a metric to be optimized. The score may represent the strength or confidence with which a face detection algorithm can detect the presence of a face within an image.

In the present embodiment, a partial face is likely to have a lower score than a complete face. A face that is viewed full-on to the viewing angle (which may be described as a face that is viewed frontally) may have a higher score than a face that is angled away from the viewing angle. A face that is upright may have a higher score than a face that not upright.

At the end of stage 66, the parameter adjustment unit 16 has determined a score for each rendering image. The score for each rendering image is the highest score that was obtained for any candidate face within the rendering image, as determined by applying the face detection algorithm to the rendering image data set that is representative of that rendering image.

At stage 68, the parameter adjustment unit 16 selects the rendering image having the highest score. In some embodiments, the parameter adjustment unit 16 may rank rendering images in order of score.

The score may be described as a quality measure. The score may reflect the confidence of the face detection. A rendering image having a high score may correspond to a high confidence that a face has been detected.

In other embodiments, a different face detection algorithm may be used. The face detection algorithm may return a score on a different scale. In some embodiments, more than one face detection algorithm is used, and the scores achieved by the different face detection algorithms are combined, for example by voting, by averaging, or by taking a maximum or minimum.

An assumption of the present embodiment is that the face detection algorithm's score is correlated with a human observer's assessment of image quality. It is assumed that the rendering image that scores the highest according to the face detection algorithm will also produce the most desirable image. However, it is possible that a human's assessment of image quality may not correlate with a particular face detection algorithm. For example, the face detection algorithm may favor rendering images rendered using harsh, face-on lighting parameters while a human may prefer softer lighting with less harsh shadows. In some embodiments, a face detection algorithm is trained to favor images that are appealing to human experts. For example, a face detection algorithm may be trained on fetal face images that have previously been selected by sonographers or parents.

In a further embodiment, the parameter adjustment unit 16 comprises a face detection module and an image quality assessment module. For each rendering image, the face detection module applies a face detection algorithm to the rendering image data set and returns a score. The image quality assessment module applies an image quality assessment algorithm to the rendering image data set and returns a further score. The image quality assessment algorithm may be configured to evaluate aesthetic image quality (the evaluation of aesthetic image quality is discussed in, for example, Shehroz S. Khan and Daniel Vogel, Evaluating visual aesthetics in photographic portraiture, CAe '12 Proceedings of the Eighth Annual Symposium on Computational Aesthetics in Graphics, Visualization and Imaging, pages 55 to 62). The further score may be described as an aesthetic image quality score. The parameter adjustment unit 16 combines the face detection score from the face detection module and the aesthetic image quality score from the image quality assessment module, and selects a rendering image based on the combined score. The combined score may be described as a quality measure.

At stage 70, the parameter adjustment unit 16 determines a roll value and a yaw value by selecting the roll value and the yaw value that were used to render the selected rendering image (the rendering image that had the highest score). In other embodiments, the parameter adjustment unit 16 determines any at least one rendering parameter value from the selected rendering image data set. For example, in one embodiment, the plurality of rendering images that are rendered at stage 64 have different lighting angles, and at stage 70 the parameter adjustment unit 16 determines a lighting angle by selecting the lighting angle used in rendering the rendering image that has the highest score. Where values for some parameters were the same in all the rendering images that were rendered at stage 64, the parameter adjustment unit 16 may continue to use those parameter values.

In the present embodiment, the parameter values of stage 70 are determined by selecting or adjusting the value of at least one of the parameters of stage 58 based on the selection of a rendering image at stage 68. In other embodiments, any suitable method of selecting or adjusting the value of at least one of the parameters may be used.

At stage 72, the volume rendering unit 14 generates a new rendering image using the determined parameters and the display control unit 19 displays the new rendering image on main display screen 19. In the present embodiment, the new volume rendering image is the selected rendering image. The displayed image has the pixel color and/or intensity values (for example, RGB or HSL values) that are specified in the selected rendering image data set.

In other embodiments, the rendering unit 14 generates the new rendering image by performing a further rendering process using the determined parameters. For example, in some embodiments the rendering unit 14 creates a new rendering image data set by rendering the volume data set using the determined parameters.

In some embodiments, the new rendering image may also or alternatively be printed, for example so that the image may be given to the patient. In some embodiments, the new rendering image data set may be stored (for example, in a file or on a removable storage medium) or exported.

At stage 74, further raw ultrasound data is obtained. In the present embodiment, ultrasound data from the probe is taken repeatedly, for example at a rate of 10 times per second. The echo signals received from the fetus vary over time, for example due to fetal movement, patient movement or probe movement. If the raw ultrasound data obtained at stage 60 is taken over a first time interval, the further raw ultrasound data of stage 74 may be taken over a second or subsequent time interval.

The further raw ultrasound data is processed to obtain a further volume data set.

At stage 76, the rendering unit 14 uses the values for roll and yaw angle that were determined at stage 70 to process the further volume data set to obtain a further rendering image. In the present embodiment, the rendering unit 14 generates only one further rendering image at stage 76. The display control unit 19 displays the further rendering image on main display screen 6.

Therefore, in the present embodiment, rendering parameter values that are determined from an image optimization process on a first set of volume data are used in rendering a second set (and possibly subsequent sets) of volume data. By generating a plurality of rendering images which have different values for roll and yaw angle and selecting the rendering image having the highest face detection score, a better facial image may be obtained than would be obtained if only a single roll angle and yaw angle were used. The resulting rendering image may be described as an optimized image. The optimized image may be obtained and displayed without the sonographer 30 having to make manual adjustments to the roll and yaw angles during measurement (although the sonographer 30 may make manual adjustments to the roll and yaw angles during measurement if desired).

In further embodiments, the rendering unit 14 may render a plurality of rendering images that have different values for any at least one rendering parameter. For example, in one embodiment the rendering unit 14 renders a plurality of rendering images using different values for a shading parameter. The parameter adjustment unit 16 runs a face detection algorithm on each rendering image data set to return a score for each rendering image data set, and selects the rendering image with the highest score. The selected rendering image is displayed on main display screen 6. The selected rendering image may be considered to have the best image quality of the various differently-shaded rendering images.

By performing automated image optimization, the system of FIG. 2 may in some cases reduce the amount of effort that an operating sonographer 30 needs to expend in manipulating ultrasound console controls during fetal keepsake imaging. A reduction in effort in manipulating ultrasound console controls may allow the sonographer to concentrate on optimizing probe positioning and on communication with clients.

The image optimization process may be computationally efficient. The image optimization process comprises face detection which is performed on rendering images by applying a face detection algorithm to rendering image data sets. The rendering image data sets are two-dimensional data sets that are representative of the pixels in an image. Operating on a two-dimensional data set may be considerably faster than operating on a three-dimensional data set (for example the volume data). It may be possible to use an object detection that performs an exhaustive search on a two-dimensional data set (such as the rendering image data set) in cases where it would not be computationally practicable to perform exhaustive search on a three-dimensional data set. Using a computationally efficient method may make the image optimization process suitable for real time operation.

Furthermore, the scores that are returned by the face detection algorithm may directly reflect the quality of the face in the rendering image. It may not be necessary to determine, for example, positions of particular facial landmarks or the exact orientation of the face in three dimensions.

The image optimization method may be used to optimize many different rendering parameters that may influence the quality of visualization, and may not be restricted to optimizing a rendering orientation. Any rendering parameter may be optimized if changing a value for that rendering parameter would change the resulting image such as to change the face detection score. For example, rendering images with different lighting and shadows may change the face detection score for those images.

In some embodiments, image optimization is performed on, for example, every second volume data set, every fifth volume data set, or every tenth volume data set. Rendering parameter values resulting from an image optimization may be used in rendering subsequent volume data sets until a further image optimization is performed.

In some embodiments, only a single image optimization is performed. In some embodiments, the sonographer 30 adjusts the position of the probe 4 and adjusts parameter values using the scanner console 10, for example to navigate to an approximately correct viewing angle. The sonographer 30 then triggers an optimization process, for example by pressing a button on scanner console 10 or entering a command using a mouse, keyboard and trackball. In some embodiments, the sonographer 30 triggers an optimization process by pressing a button or a foot pedal or by operating some other trigger, for example by giving a voice command to a voice detection system.

For example, the sonographer 30 may concentrate on finding a good probe position and pressure. When the sonographer 30 is satisfied with the probe position and pressure, the sonographer 30 presses a button to initiate optimization. In one embodiment, the optimization comprises stages 62 to 70 of FIG. 4. The optimization is performed on the raw ultrasound data that had most recently been acquired at the time that the sonographer 30 triggered the optimization. The optimization comprises processing the raw ultrasound data to obtain volume data, rendering a plurality of image data sets from the volume data, performing face detection on each rendering image data set to determine a score for each rendering image data set, selecting the one of the rendering image data sets that has the highest score and determining parameter values from the selected rendering image data set.

The determination of parameters using the process of stages 62 to 70 of FIG. 4 may correspond, for example, to a process of spinning round and optimally lighting the captured volume to achieve the best possible view of the fetal face. The parameter values determined during the optimization may continue to be used unless or until the sonographer 30 triggers a further optimization. For example, rendering parameters that have been determined using the optimization may be used for rendering all subsequent volume data sets until a further optimization is performed. In one embodiment, the sonographer triggers an optimization in which rendering images are rendered with a range of different rendering orientations and lighting positions. The optimization results in the determination of particular rendering orientation and lighting position parameters. The determined rendering orientation and lighting position parameters are used to render each subsequent volume data set until a further optimization is performed.

In some embodiments, image optimization may be performed on every volume data set that is generated by the volume generating unit 18. In some embodiments, a continuously running optimization program (which may be referred to as a wizard) is used to optimize one or more rendering parameters repeatedly during an ultrasound scan. For example, the parameter adjustment unit 16 may perform stages 62 to 70 of FIG. 4 on every set of raw ultrasound data that is acquired by the ultrasound machine. The optimization program may automatically optimize view parameters and lighting parameters while the sonographer 30 conducts the scan, for example while the sonographer 30 adjusts the position of the probe 4.

In one embodiment, roll and yaw angles are determined at stage 70 from a plurality of rendering image data sets representative of rendering images that were rendered from a first volume data set acquired at a first time interval. Further raw ultrasound data acquired at a second time interval is obtained at stage 74 and is processed to generate further volume data. A plurality of further rendering images is rendered from the further volume data at stage 76. One of the plurality of further rendering images has the values for roll and yaw angle that were determined from the rendering image data sets at stage 70, and the other further rendering images have values for roll and yaw angle that have been varied from the determined values for roll and yaw angle, such that the rendering images that have been rendered from the further volume data have a plurality of values of roll angle and yaw angle. The values of roll angle and yaw angle may be centered around the roll angle and yaw angle that were determined at stage 70.

Stages 66 to 72 are repeated to select the one of the further rendering images having the face detection score, determine a new roll and yaw angle from the selected further rendering images, and display the further rendered image having the new roll and yaw angles. The newly determined roll and yaw angles may then be used in rendering a next set of volume data that is acquired over a third time interval.

The optimization method of FIG. 3 or FIG. 4 may be performed on a continuous feed of ultrasound volumes, or on a single volume. Repeated optimization may be performed. For the single volume, in some embodiments a single optimization may be performed. In other embodiments, repeated optimizations of a single volume may be performed, for example while the sonographer 30 is manually varying one or more parameters.

Figure 5:
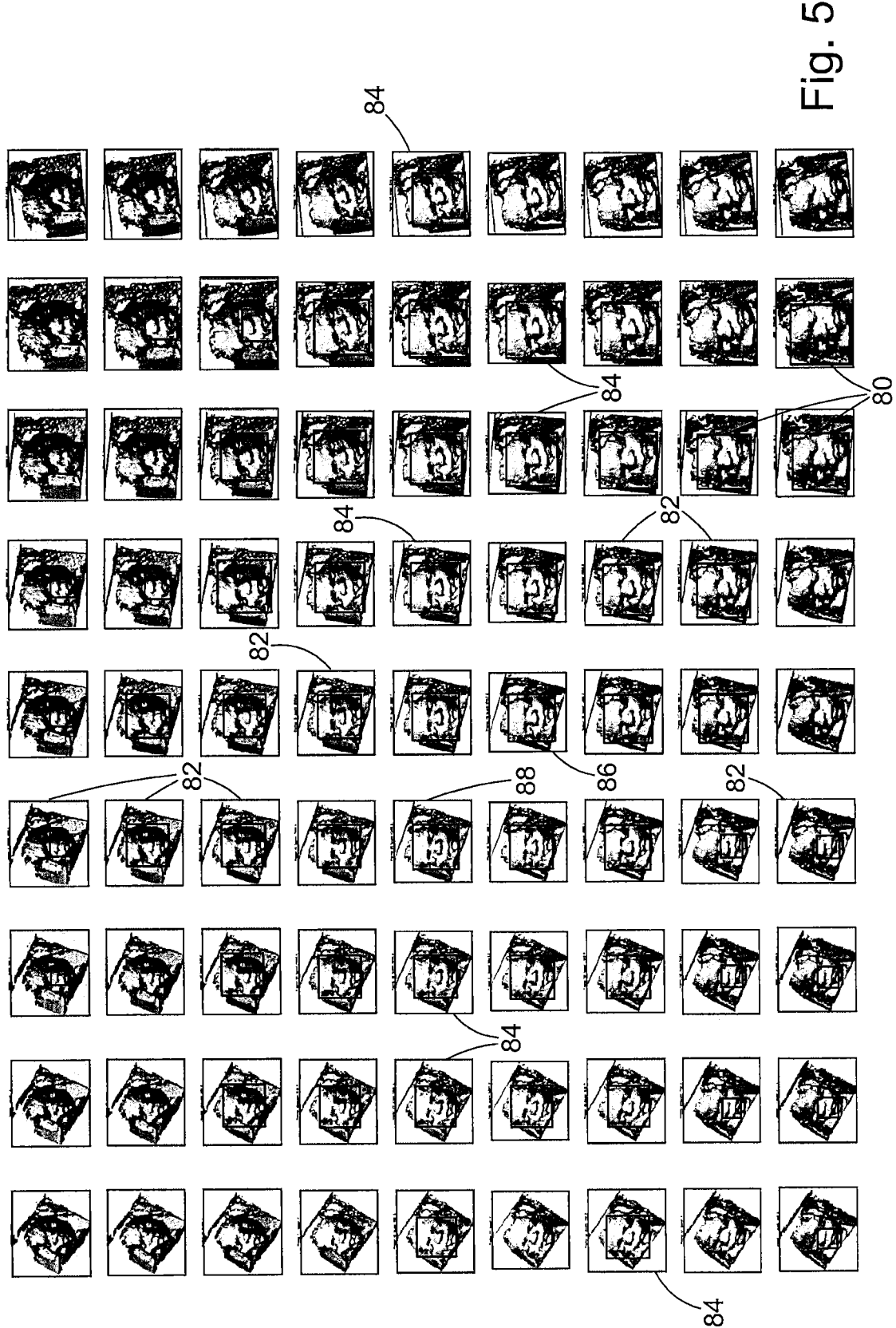
FIG. 5 is a matrix of facial images that have been assessed using a face detection algorithm.

FIG. 5 shows a plurality of facial rendering images, arranged as a matrix. Each of the rendering images corresponds to a respective rendering image data set. All of the rendering images of FIG. 5 are simple surface-shaded renderings of the same volume data set, but with different values for roll and yaw of the viewing angle.

On the matrix of images in FIG. 5, images in different columns have different values for roll of viewing angle and images in different columns have different values for yaw of viewing angle. Each rendering image has a unique combination of roll and yaw values.

A face detection algorithm (in this case, the Open CV face detection algorithm) was used to perform face detection in each of the rendering image data sets corresponding to a respective rendering image in FIG. 5. A score for each rendering image data set was obtained from the face detection algorithm. In the discussion below, a score is associated with each rendering image. The score associated with a rendering image may be taken to be the score that has been determined for the corresponding rendering image data set.

For each rendering image for which a face was found by the face detection algorithm in the rendering image data set, a box 80 representing the position and extent of the face as determined by the face detection algorithm is shown on the rendering image in FIG. 5.

FIG. 5 has been marked up to show which images are associated with high scores. Each image indicated by reference numeral 82 has the highest score of any image in its row. Each image indicated by reference numeral 84 has the highest score of any image in its column. Image 86 has the highest score of any image in its row and also the highest score of any image in its column. Image 88 is the image that has the highest score of any image in the matrix.

Figure 6:
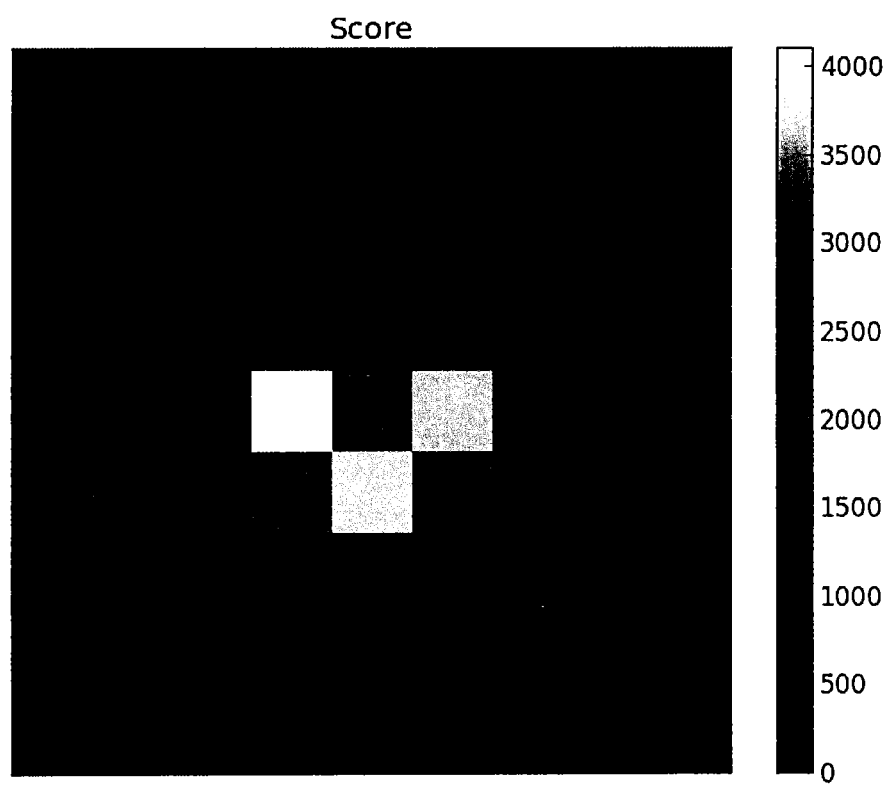
FIG. 6 is a heat map display of the face detection algorithm's score for each of the matrix of facial images in FIG. 5.

FIG. 6 is a heat map diagram representing the score for each of the images of FIG. 5. Each image is represented by a box having a position corresponding to the position of that image in the matrix. Each box is colored in dependence on the score for that image, with a scale of greyscale values representing scores from 0 to over 4000 (the highest score, which may be considered to correspond to the best face). Boxes whose color is towards the black end of the scale represent images having a low score. Boxes whose color is towards the white end of the scale represent images having a high score.

The heat map shows the face detection algorithm's scores for the matrix of images in FIG. 5. By comparing the heat map to the facial images of FIG. 5, it can be seen that the highest scores of FIGS. 5 and 6 were achieved by face-on, upright orientations.

Different quality measures (for example, different face detection scores, image quality assessment scores, or combinations of scores) may be used in different embodiments. In some embodiments, the face detection algorithm is a trained classifier. The classifier may be trained on images that have been determined (for example, manually determined) to be good or bad faces (or not to be faces at all). In other embodiments, any suitable method of face detection may be used.

In the embodiment of FIG. 2, the face detection algorithm is trained on face images that are not fetal face images. In other embodiments, the face detection algorithm is trained on fetal face images. In some circumstances, an algorithm that is specifically trained on fetal face images may achieve better fetal face detection and/or assessment of fetal face image quality than an algorithm that is trained on non-fetal face images.

The above embodiments may use a face detection algorithm which has previously been trained to detect facial images (optionally, fetal face images), and is implemented in the image optimization described above without any changes being made to the face detection algorithm. However, in other embodiments, the face detection algorithm may continue to learn while being used in repeated instances of the image optimization process. For example, the sonographer 30 may select facial images during measurement, for example by freeze framing or performing an image capture. The face detection algorithm may assume that the sonographer 30 only selects good faces, and may therefore add the images selected by the sonographer 30 to its training set of good faces.

The definition of the quality measure and/or the image data sets on which any face detection algorithm is trained may reflect various requirements for the facial image.

Face detectors (for example, the OpenCV face detector) may be expected to optimize towards presenting faces upright and viewed frontally. If there is obscuring matter in front of the face, the system may prefer viewpoints from which the face is fully visible in preference to viewpoints from which the face is obscured.

In many embodiments the value for a quality measure may be higher for images where the entire face is visible than for a similar face (for example, a face of similar size and resolution) that is partially obscured. The system may prefer viewpoints from which the whole face is visible to images in which only a portion of the face is visible. In some embodiments, the value for the quality measure may be higher for an upright face than for a face that is tilted away from upright. In some embodiments, the value for the quality measure may be higher for a face that fully faces the viewing angle than for one that is angled away.

In some embodiments, the face detection algorithm determines a location of the face. In some embodiments, the value for the quality measure may be higher for faces located near the center of the image than for those located at the periphery. For example, in one embodiment, the face detection algorithm outputs a location and score for a candidate face, and the parameter adjustment unit 16 obtains a quality measure for that candidate face by weighting the score by a weighting that is determined in dependence on the location. The face detection algorithm may determine a size of the face. In some cases, the value for the quality measure may be higher for a face that occupies a certain proportion of the image, for example 60% of the image, than for images that occupy a greater or lesser proportion of the image.

In some embodiments, the quality measure is dependent on aspects of the image such as lighting, color balance, contrast, or sharpness. In some embodiments, a face detection algorithm is trained to return the highest value for the quality measure for straight-on lighting. In other embodiments, another lighting angle may be preferred.

In some embodiments, more than one quality measure is determined for each image (for example, a measure of location and a measure of size), and the quality measures are combined to give an overall quality measure.

Although in the embodiments described above a high value for the quality measure indicates a good image, in alternative embodiments a low value for the quality measure may indicate a good image.

In the embodiments above, a high quality measure may be obtained when the fetal face fully faces the viewing angle. However, in some embodiments, it may be desirable to view the fetal face at a different angle, for example in profile or angled to the side.

In some embodiments, a classifier is trained such that faces in profile, in three-quarter view, or at an appropriate angle produce the highest quality measure. For example, OpenCV has a face profile detector.

In other embodiments, at stage 68 the parameter adjustment unit 16 selects a rendering image data set using a face detection algorithm that favors faces that fully face the viewing position. At stage 70 the parameter adjustment unit 16 determines rendering orientation parameter values from the selected rendering image data set. The parameter adjustment unit 16 then applies an offset to the determined parameter values to rotate the view, for example to rotate the view by 30°, 45° or 90°, to obtain a different view of the fetal face. At stage 72, the rendering unit 14 generates a new rendering image data set using the parameters to which an offset has been applied, and displays the new rendering image on main display screen 6.

Similar offsets may be applied to any determined parameters (for example, lighting parameters or shading parameters). Offsets may be applied automatically by parameter adjustment unit 16. In some embodiments, offsets may be applied by the sonographer 30.

In the embodiments above, a method of image optimization is described in which a plurality of rendering image data sets are generated at stage 64, face detection is performed on each rendering image data set at stage 66, and a rendering image data set is selected at stage 68 based on image quality, for example based on a face detection score.

The method of image optimization described above may be described as a brute-force method of searching a parameter space by generating rendering images at different places in the parameter space (for example, having different values of the parameters for roll angle and yaw angle) and obtaining a value for a quality measure for each of the rendering image data sets In other embodiments, any suitable process of image optimization may be used, which may or may not be a brute-force method. The parameter adjustment unit 16 may select a rendering image (or may select one or more parameters, for example roll angle or yaw angle) by using any suitable optimization process to optimize the quality measure. For example, the parameter adjustment unit 16 may optimize the quality measure using hill-climbing to improve the image appearance from initial settings.

The parameter adjustment unit 16 may work in conjunction with the rendering unit 14 to iteratively explore the space of possible images, and identify the best one according to the selected object detector (for example, according to the score that is output by the face detection algorithm).

In one embodiment, at stage 64, the rendering unit 14 generates a rendering image using parameter values that were determined at stage 58. At stage 66, the parameter adjustment unit 16 performs face detection on the rendering image, thus determining a score for the rendering image.

The parameter adjustment unit 16 then adjusts at least one of the parameter values (for example, increases roll angle).

The process returns to stage 64 and a new rendering image is generated using the adjusted parameter. At stage 66 the parameter adjustment unit 16 performs face detection on the new rendering image and determines a score for the new rendering image.

If the score for the new rendering image is greater than the score for the original rendering image, the parameter adjustment unit 16 may continue to adjust the parameter in the same direction (for example, continuing to increase the roll angle). If the score for the new rendering image is lower than the score for the original rendering image, the parameter adjustment unit 16 may adjust the parameter in the opposite direction from the previous adjustment (for example, decrease the roll angle). The process returns to stage 64 to render another rendering image from the volume data using the newly adjusted parameter.

Stages 64 and 66 may be repeated until a local maximum score is found. When a local maximum is found, the rendering image having that score is selected at stage 68. Parameter values relating to the selected rendering image are determined at stage 70, and an image having those parameter values is displayed at stage 72.

In some embodiments, a threshold for quality measure may be used. In one such embodiment, a rendering image is generated at stage 64 using the parameter values that were determined at stage 58. At stage 66, the parameter adjustment unit 16 performs face detection and outputs a value for a quality measure. The parameter adjustment unit 16 compares the value for quality measure to a threshold value. In one embodiment, the quality measure is the score from the face detection algorithm as shown in FIG. 6, and the threshold value for the quality measure is 4000. If the value for the quality measure is greater than the threshold, the parameter optimization unit 16 selects the rendering image and no further rendering images are generated. If the value for the quality measure is below the threshold, any suitable image optimization method may be performed until a rendering image is produced that has a value for the quality measure above the threshold. When a rendering image is produced that has a value for the quality measure that is above the threshold, that rendering image is selected at stage 68.

In some embodiments, an iterative version of a brute-force method may be used. In one embodiment, the rendering unit 14 generates a plurality of rendering images by incrementing values for roll angle and yaw angle by increments of 10°. The parameter adjustment unit 16 performs face detection on each of the rendering images and selects the rendering image having the highest score. The parameter adjustment unit 16 determines the roll angle and yaw angle of the selected rendering image and passes the values back to the rendering unit 14.

The rendering unit 14 then generates a further plurality of rendering images by incrementing the roll angle and yaw angle for the selected rendering image by 1°. The parameter adjustment unit 16 performs face detection on each of the further plurality of rendering images, and selects the one of the further plurality of rendering images that has the highest score. The display control unit 19 displays the selected one of the further plurality of rendering images on main display screen 6.

In another iterative embodiment, different parameters are varied at different stages of iteration. For example, a first stage is performed in which rendering images with different roll and yaw angles are generated, face detection is performed, a rendering image is selected, and roll and yaw angles for the selected rendering image are determined.

The determined roll and yaw angles are passed back to the rendering unit 14, and the rendering unit 14 generates a further plurality of rendering images in which all of the rendering images have the determined roll and yaw angles, but the lighting angle is varied. The parameter adjustment unit 16 performs face detection and selects one of the further plurality of rendering images. The display control unit 19 displays the selected one of the further plurality of rendering images on main display screen 6.

Although the embodiments above describe two iterations of the process of stages 64 to 68, in further embodiments any number of iterations of the process of stages 64 to 68 may be used.

Although the embodiments above focus primarily on varying roll and yaw angle, these embodiments are by way of example, and in other embodiments, any rendering parameters may be used. Rendering parameters may include pitch angle, or any other parameter affecting the positioning of the subject in three-dimensional space.

Any rendering parameter or combination of rendering parameters may be varied in order to generate a plurality of rendering images from the volume data set at stage 64. Any rendering parameter or combination of rendering parameters may be determined from the selected rendering image at stage 70.

Rendering parameters may include one or more optical properties of the volume being rendered such as opacity and/or scattering or reflection coefficients or parameters of more advanced rendering models. Rendering parameters may include ambient, diffuse or specular coefficients. Rendering parameters may include illumination direction, lighting parameters, view parameters, shading parameters, iso-surface value or clip plane position.

A rendering image may be rendered so as to add Depth of Field to the rendering image. Depth of Field is a parameter that may be heavily used in photographic portraiture, and may add an aesthetically appealing effect to a fetal image. When Depth of Field is added to a rendering image, the rendering image may have some areas (particularly the fetal face) in sharp focus, and other areas in less sharp focus. Depth of Field may be a parameter that is varied and selected using the method of FIG. 4.

In some embodiments, rendering images may be rendered using more than one image rendering method. For example, rendering images may be rendered with and without global illumination. The face detection algorithm may return a score for the rendering images with and without global illumination and may select a rendering image with or without global illumination in dependence on the score.

In many of the embodiments above, a plurality of rendering images are generated, one of the rendering images is selected, and the parameter values determined in stage 70 are the parameter values that were used to render the selected rendering image. However, in alternative embodiments, the parameter values determined at stage 70 may not be the parameter values used to render one of the rendering images. For example, parameter values may be selected that are an average of parameter values for the best rendering images (for example, an average of values for the top three data sets) or that are interpolated between those for the best rendering images (for example, as part of an optimization process). Parameter values may be altered after stage 70, for example by applying an offset.

In embodiments above, the rendering unit 14 generates a plurality of rendering images which are each rendered from the same volume data set.

In further embodiments, rendering images are rendered from different volume data sets.

In some embodiments, a first set of raw ultrasound data (for example, from a first time interval) is processed by the volume data generating unit 18 to produce a first volume data set. A second set of raw ultrasound data (for example, from a second time interval) is processed by the volume data generating unit 18 to produce a second volume data set. The rendering unit 14 processes the first volume data set to produce at least one rendering image, and processes the second volume data set to produce at least one rendering image.

All of the rendering image data sets for the rendering images (whether produced from the first or the second volume data set) are then passed to the parameter adjustment unit 16 and face detection is performed on each rendering image data set. One of the rendering image data sets is selected as having the highest quality measure. The selected rendering image data set may come from either volume data set.

In the flow chart of FIG. 4, stage 62 comprises the processing of raw ultrasound data (echo signals obtained through ultrasonic transmission and reception to and from a three-dimensional region of interest in the patient) to generate volume data. The processing is based on a plurality of processing parameters. Processing parameters may include, for example, echo-processing controls, reconstruction parameters, signal parameters, volume parameters and filtering parameters.

In some embodiments, different processing parameters are used to process one or more sets of raw ultrasound data to obtain multiple sets of volume data. The sets of volume data are then rendered to obtain rendering images, and object detection (for example, face detection) is performed to select one of the rendering images. Processing parameters are then determined from the selected rendering image, and may be used in the processing of subsequent raw ultrasound data.

In one embodiment, a set of raw ultrasound data is processed using a first set of processing parameters to produce a first set of volume data. The same set of raw ultrasound data is processed using a second set of processing parameters to produce a second set of volume data. The rendering unit 14 processes the first volume data set to produce a first rendering image data set, and processes the second volume data set to produce a second rendering image data set. The parameter adjustment unit 16 performs face detection on the first and on the second rendering image data set, to obtain a score for each of the first and the second rendering image data set. The parameter adjustment unit selects the one of the first and second rendering image data sets that has the higher score (and therefore may represent a better facial image). The selected rendering image data set may come from either volume data set. In further embodiment, more than one rendering image data set is rendered from each volume data set.

In some embodiments, processing parameters of the selected rendering image data set may be determined at stage 70 in addition to or instead of the determination of rendering parameters. The determined processing parameters may then be passed to the volume data generating unit 14 and used in the processing of subsequent sets of raw ultrasound data.

In embodiments above, the parameter adjustment unit 16 selects a rendering image data set based on image quality (for example, based on a face detection score) without any input from the sonographer to the selection. In the embodiment described above with reference to FIG. 4, the sonographer 30 does not adjust any parameters using the scanner console 10 during the measurement and the image selection is fully automated.

In further embodiments, the sonographer 30 may be involved in the selection process and/or in parameter adjustment.

In some embodiments, the sonographer 30 may make adjustments to parameter values using the scanner console 10 while measurement is in progress. In some such embodiments, if a parameter value is input by the sonographer 30, the rendering unit 14 generates a rendering image using the input parameter value and the display control unit 19 displays the rendering image on main display screen 6. The rendering unit 14 and parameter adjustment unit 16 may then begin an image optimization using the sonographer's input as the starting point for the optimization.

In some embodiments, the sonographer 30 may enter a range of values for a parameter, for example by turning a dial, and rendering images may be generated using parameter values in the range that has been entered.

In some embodiments, the sonographer 30 decides whether or not to use the image optimization process. The sonographer 30 may switch between a manual mode in which image optimization is not used, and an assisted mode in which image optimization is performed. The sonographer 30 may initiate an optimization process during a scan.

In some embodiments, the sonographer 30 may perform most of the parameter adjustment manually, but final optimization of images may be performed by the system of FIG. 2.

In some embodiments, the parameter adjustment unit 16 selects more than one rendering image at stage 68. For example, the parameter adjustment unit 16 selects several rendering images each of which corresponds to a local maximum in the quality measure (for example, in the face detection score). The display control unit 19 displays the selected rendering images on control screen 8 (in other embodiments, images may be displayed on main display screen 6 or on another display screen). The sonographer 30 selects one of the displayed images, for example by using a mouse or trackball. The display control unit 19 displays the selected image on main display screen 6.

In some similar embodiments, the rendering image data set representative of the rendering image selected by the sonographer 30 may be stored (for example, in a patient file or on a removable storage medium) or exported. The rendering image selected by the sonographer 30 may be printed.

In some embodiments, image optimization is performed on each set of volume data over time, and the sonographer 30 may choose to freeze or capture the displayed image at any time. The displayed image corresponds to a selected rendering image data set. The selected rendering image data set may be stored or exported.

Although the embodiments above describe face detection, in other embodiments different body parts or portions of body parts may be detected. Detector algorithms may be trained to detect other objects and specific object orientations (for example, OpenCV has a face profile detector as well as a face detector).

In some embodiments, an ultrasound scan is performed on the abdomen of a patient 32 carrying a fetus 34. Raw ultrasound data from the scan is processed to obtain volume data, and the volume data is processed to obtain rendering images. An object detection algorithm is applied to rendering image data sets to obtain a value for a quality measure, which may be a detection score. The object detection algorithm may be an algorithm that is trained to detect any suitable part of the fetal body.

In some embodiments, a hand detection algorithm is implemented in the parameter adjustment unit 16. The hand detection algorithm may be a classifier that has been trained on images of hands. In some embodiments, the hand detection algorithm may have been trained specifically on images of fetal hands. The parameter adjustment unit 16 obtains a hand detection score for each of a plurality of rendering images, and selects the rendering image having the highest hand detection score, which may be the rendering image corresponding to the best image of the fetal hand.

In some embodiments, a foot detection algorithm is implemented in the parameter adjustment unit 16. The hand detection algorithm may be a classifier that has been trained on images of feet. In some embodiments, the hand detection algorithm may have been trained specifically on images of fetal feet. The parameter adjustment unit 16 obtains a foot detection score for each of a plurality of rendering images, and selects the rendering image having the highest foot detection score, which may be the rendering image corresponding to the best image of the fetal foot.

In embodiments in which a hand detection or foot detection algorithm is used, the hand detection or foot detection algorithm may be trained such that the score is higher if the image is clearer or if the hand or foot is more centered in the image. Any suitable quality measure or combination of quality measures may be used, for example a combination of a hand or foot detection score and an aesthetic image quality score. In some embodiments, the value for the quality measure is higher if the hand or foot is upright in the image. In other images, the quality measure does not assess whether the hand or foot is upright. In some circumstances, there may be more tolerance for non-upright images of hands or feet than for non-upright images of faces.

In some embodiments, detection algorithms may detect specific parts of the face, for example the eyes, ear, mouth or nose.

In some embodiments, detection algorithms may detect the genital region. In some embodiments, two detection algorithms are used, one trained on the genital region in males and one trained on the genital region in females. The image optimization process may be used to select a rendering image in which the genitals may be seen clearly, for example for sex determination. The value for the quality measure may be higher for images in which the genital region is clearly shown.

Conversely, in some circumstances, there may be a need to avoid showing ultrasound images in which the genital region of the fetus is present. For example, some hospitals avoid disclosing the sex of the fetus in fetal ultrasound scans, and some parents prefer not to learn the sex of the fetus through an ultrasound scan. Therefore, in the case of the genital region it may be required to obtain an image in which the genital region is not shown rather than obtaining an image in which genital region is shown clearly, In one such embodiment, the sonographer 30 sets some initial settings on the scanner console 10 (for example, viewpoint, orientation and lighting). The sonographer 30 positions the measurement probe 4 on the abdomen of the patient 32 who is carrying the fetus 34. The measurement probe 4 obtains raw ultrasound data which is processed by the volume data generating unit 18 to produce a volume data set. The rendering unit 14 generates a rendering image data set from the volume data set, using the values set by the sonographer 30.

The parameter adjustment unit 16 runs a detection algorithm on the rendering image data set, where the detection algorithm is trained to detect the genital region. If the detection algorithm returns a quality measure of zero or below a low threshold the rendering image data set is selected and the corresponding rendering image is displayed on main display screen 6.

If the detection algorithm returns a higher value for the quality measure (for example, a value for the quality measure above a given threshold value), then the rendering unit 14 generates a plurality of rendering images, for example a plurality of rendering images each having a different viewpoint. The parameter adjustment unit 16 runs the detection algorithm on each of the rendering image data sets corresponding to the rendering images.

In some embodiments, the rendering image having the lowest value for the quality measure is displayed. In other embodiments, the rendering image having the lowest value for the quality measure is displayed only if the value for the quality measure is below a given threshold (or in some embodiments, if the value for the quality measure is zero). If the value for the quality measure is above the threshold, further rendering images are generated and detection performed until a rendering image having a low enough value for the quality measure is obtained.

Although the above embodiment is described as a process of minimizing the quality measure, in other embodiments the detection algorithm may be trained such that a high value for the quality measure is achieved by a rendering image corresponding to an image that does not show the genital region.

For example, in some embodiments, a high value for the quality measure is achieved by a rendering image that is clear and centered, but does not show the genital region.

In some embodiments, the detection algorithm for the genital region is used in addition to other detection algorithms. For example, in one embodiment for obtaining an image of a foot, a foot detection algorithm and the detection algorithm for the genital region are both used. A plurality of rendering images is generated at stage 64. The detection algorithm for the genital region is used to rule out rendering images in which the genital region is shown, and then the foot detection algorithm is used to select the best one of the remaining rendering images.

In other embodiments, any combination of detection algorithms may be used. For example, hand and face detection algorithms may be used together to obtain an image in which both the hand and the face are shown.

In some embodiments, the parameter adjustment unit 16 may use two or more detection algorithms on the rendering images to select two or more of the rendering images for display. For example, the parameter adjustment unit 16 may select one image that has the best face detection quality measure and one image (which may be a different image) that has the best hand detection quality measure. In another embodiment, the parameter adjustment unit 16 may select one image that has the best quality measure for a full-on face and one image that has the best quality measure for a face in profile.

In some embodiments, an ultrasound scan is performed on a body part of a patient to image the body part of that patient, for example to perform diagnosis or monitoring. In one embodiment, the kidney of a patient is scanned using an ultrasound scanner 2 and probe 4. Raw ultrasound data obtained from the kidney scanned is processed by the volume data generating unit 18 to generate volume data. The rendering unit 14 renders multiple rendering images from the volume data by varying rendering parameters. The parameter adjustment unit 16 runs a kidney detection algorithm on each of the rendering image data sets. The kidney detection algorithm is trained so that it returns a high score if the kidney is rendered in a desirable orientation for viewing, for example if the rendering parameters are such that the kidney is displayed in a standard viewing orientation. A standard viewing orientation for the kidney may be an orientation that is defined relative to the kidney's own axes rather than to the axes of the patient's body.

The parameter adjustment unit 16 selects the rendering image that has the highest score, and therefore may correspond to the best viewing orientation for the kidney. The display control unit 19 displays the selected rendering image on main display screen 6. Parameters of the selected rendering image (for example, rendering orientation parameters) may be used in rendering subsequent sets of volume data.

In further embodiments, an ultrasound scan is performed on the heart of a patient. In one embodiment, a detection algorithm is used that detects a particular orientation of the heart (for example, a standard viewing orientation relative to the axes of the heart). In other embodiments, a detection algorithm is used that detects a particular part of the heart, or a cardiac blood vessel.

In alternative embodiments, any suitable part of the body (for example, any internal organ) may be scanned and detected. For example, a uterus or ovary may be scanned and detected. In some embodiments, a part of the body is scanned and a pathology is detected. For example, in one embodiment, the gall bladder is scanned and a gall stone detection algorithm is used to detect gall stones. In such an embodiment, the parameter adjustment unit 16 may use the gall stone detection algorithm to obtain a score for each of plurality of rendering images, and the rendering image data set with the highest score (which may correspond to the best view of one or more gall stones) may be selected. The detection algorithms that may be used for other parts of the body may be similar or the same as those used for face detection, but trained on sets of image data representing the body part in question, or may be dedicated detection algorithms for those other parts of the body.

The above embodiments have described the use of detection algorithms to perform image optimization of ultrasound data while the ultrasound data is being taken. In further embodiments, detection algorithms may be used to perform image optimization of stored data, for example to process stored ultrasound data to obtain the best possible facial image. In some such embodiments, some or all of the stages of FIG. 4 may be performed using, for example, a PC or workstation rather than an ultrasound machine 2.

Rendering images may comprise images derived from a surface rendering or volume rendering process. The use of a detection algorithm on a rendering image may comprise the use of a detection algorithm on a rendering image data set that is representative of that rendering image. Similarly, the generation of a rendering image may comprise the generation of a rendering image data set. References to rendering images do not necessarily imply that the rendering images are displayed. Rendering image data sets representative of the rendering images may be processed without display of the rendering images.

Certain embodiments provide an apparatus comprising an ultrasound scanner, a 3D rendering unit and a display in which selected parameters of the various control parameters influencing the displayed image are under the control of an image optimizing unit. The image optimizing unit is responsible for identifying the presence of a face in the displayed image, and for determining the image quality of that face according to a programmed metric. The optimization unit adjusts the parameters under its control so as to optimize the quality metric.

The parameters may include view position and orientation. The parameters may include any of illumination direction, simulated material optical properties, lighting model parameters, echo-processing controls, isosurface values, signal parameters, volume parameters, view parameters, filtering parameters.

The apparatus may alternatively or additionally detect the discernibility and rendered image quality of other anatomy such as hands or feet.

The automatically optimized parameters may be taken as a baseline to which operator controlled programmed-in offsets may be applied.

Whilst particular units have been described herein, in alternative embodiments functionality of one or more of these units can be provided by a single processing resource or other component, or functionality provided by a single unit can be provided by two or more processing resources or other components in combination. Reference to a single unit encompasses multiple components providing the functionality of that unit, whether or not such components are remote from one another, and reference to multiple units encompasses a single component providing the functionality of those units.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An ultrasonic imaging apparatus, comprising: processing circuitry configured to
   generate volume data by processing echo signals obtained through ultrasonic transmission and reception to and from a three-dimensional region including at least a portion of a body part;
   generate a plurality of two-dimensional rendering images by performing a rendering process on the volume data based on a plurality of parameters, each rendering image based on a different value of at least one of the plurality of parameters, the at least one parameter including a parameter related to a rendering orientation;
   perform a detection of the at least a portion of the body part in each of the plurality of two-dimensional rendering images by applying an object detection algorithm and generating a respective detection score for each of the plurality of rendering images based on a result of the detection;
   select at least one of the plurality of rendering images based on the detection scores;
   adjust a value of at least one parameter of the plurality of parameters relating to the selected rendering image;
   generate a new rendering image based on the adjusted value of the at least one parameter; and
   display the new rendering image on a display.

2. The ultrasonic imaging apparatus according to claim 1, wherein the body part is a body part of a fetus.

3. The ultrasonic imaging apparatus according to claim 2, wherein the body part of the fetus comprises at least one of a face, a head, an eye, a nose, a mouth, an ear, a hand, a foot, and a genital region.

4. The ultrasonic imaging apparatus according to claim 1, wherein the body part comprises at least one of an organ, an internal organ, a heart, a kidney, a uterus, and an ovary.

5. The ultrasonic imaging apparatus according to claim 1, wherein the adjusting the value of at least one parameter of the plurality of parameters is based on image quality of a representation of the at least a portion of the body part in the selected rendering image.

6. The ultrasonic imaging apparatus according to claim 1, wherein the adjusting the value of at least one parameter of the plurality of parameters comprises the processing circuitry or adjusting the value of the at least one parameter in order to optimize image quality of the representation of the detected at least a portion of the body part.

7. The ultrasonic imaging apparatus according to claim 6, wherein the processing circuitry is further configured to evaluate the image quality in accordance with a predetermined method of measurement.

8. The ultrasonic imaging apparatus according to claim 1, wherein the body part comprises a face of a fetus, wherein the detection by the processing circuitry comprises face detection, and wherein the detection score comprises a face detection score.

9. The ultrasonic imaging apparatus according to claim 1, wherein the result of the detection by the processing circuitry comprises at least one candidate object location and at least one associated detection score.

10. The ultrasonic imaging apparatus according to claim 1, wherein the object detection algorithm executed by the processing circuitry comprises at least one of a Viola-Jones object detection framework, a classifier, a cascade of boosted classifiers, a neural network, a genetic algorithm, and co-occurrence histograms of oriented gradients.

11. The ultrasonic imaging apparatus according to claim 1, wherein the detection score is dependent on at least one of:
   whether the at least a portion of the body part is visible;
   whether the at least a portion of the body part is upright;

whether the at least a portion of the body part is frontal;
a location of the at least a portion of the body part;
a size of the at least a portion of the body part;
symmetry of the at least a portion of the body part; and
an orientation of the at least a portion of the body part.

12. The ultrasonic imaging apparatus according to claim 1, wherein the plurality of parameters comprise at least one of an echo-processing control, a reconstruction parameter, a signal parameter, a volume parameter, and a filtering parameter.

13. The ultrasonic imaging apparatus according to claim 1, wherein the plurality of parameters comprises at least one of a rendering orientation parameter, an illumination direction, an optical property, a lighting parameter, an isosurface value, a shading parameter, a position of a clip plane, an opacity, a scattering coefficient, a reflection coefficient, a parameter of an advanced rendering model, an ambient coefficient, a diffuse coefficient, a specular coefficient, and a depth of field.

14. The ultrasonic imaging apparatus according to claim 1, wherein the echo signals are time-varying signals, and wherein the processing circuitry is further configured to generate the rendering images from volume data representative of signals received at a first time, and to generate the new rendering image from volume data representative of signals received at a second time.

15. The ultrasonic imaging apparatus according to claim 1, wherein the detection score for each rendering image is representative of an image quality of the at least a portion of the body part in the rendering image.

16. The ultrasonic imaging apparatus according to claim 1, wherein the detection score for each of the rendering images comprises values for a plurality of measures of image quality, and wherein the adjusting of the at least one parameter of the plurality of parameters is based on a combination of the values for the plurality of measures of image quality.

17. The ultrasonic imaging apparatus according to claim 16, wherein the plurality of measures of image quality comprises at least one body part detection score and at least one aesthetic image quality score.

18. The ultrasonic imaging apparatus according to claim 1, wherein the processing circuitry is further configured to generate the new rendering image by performing the rendering process on the volume data based on the adjusted value of the at least one parameter.

19. The ultrasonic imaging apparatus according to claim 1, wherein the processing circuitry is further configured to generate the plurality of rendering images in response to user input and perform the detection of the at least one body part in the plurality of rendering images in response to the user input.

20. An ultrasonic imaging method, comprising:
generating volume data by processing echo signals obtained through ultrasonic transmission and reception to and from a three dimensional region including at least a portion of a body part;
generating a plurality of two-dimensional rendering images by performing a rendering process on the volume data based on a plurality of parameters, each rendering image based on a different value of at least one of the plurality of parameters, the at least one parameter including a parameter related to a rendering orientation;
performing a detection of the at least a portion of the body part in each two-dimensional rendering images by applying an object detection algorithm and generating a respective detection score for each of the plurality of rendering images based on a result of the detection;
selecting at least one of the plurality of rendering images based on the detection scores;
adjusting a value of at least one parameter of the plurality of parameters relating to the selected rendering image;
generating a new rendering image based on the adjusted value of the at least one parameter; and
displaying the new rendering image on a display.

21. A non-transitory computer-readable storage medium storing a computer program for causing processing circuitry to perform the method according to claim 20.

* * * * *